United States Patent [19]

White, Jr. et al.

[11] 4,273,927

[45] Jun. 16, 1981

[54] CONVERTING ENZYME INHIBITOR

[75] Inventors: Ralph L. White, Jr.; David E. Portlock, both of Norwich, N.Y.

[73] Assignee: Morton-Norwich Products, Inc., Norwich, N.Y.

[21] Appl. No.: 177,905

[22] Filed: Aug. 14, 1980

[51] Int. Cl.³ .......................................... C07D 513/04
[52] U.S. Cl. ..................................................... 544/32
[58] Field of Search ........................................ 544/32

[56] References Cited

PUBLICATIONS

Neelakantan et al., Chemical Abstracts, vol. 80, entry 82872z (1974).

*Primary Examiner*—John M. Ford
*Attorney, Agent, or Firm*—Anthony J. Franze

[57] ABSTRACT

The compound 5,6-dihydro[1,4]thiazino[4,3-a]quinoline-1(2H),4(4aH)-dione is useful as an angiotensin converting enzyme inhibitor.

1 Claim, No Drawings

CONVERTING ENZYME INHIBITOR

This invention is concerned with the compound 5,6-dihydro[1,4]thiazino-[4,3-a]quinoline-1(2H),4(4aH)dione. It is useful as an inhibitor of the enzyme responsible for converting angiotensin I to angiotensin II.

Of late, it has been recognized that a substance capable of interrupting the pathway whereby angiotensin II is produced, vis.; the conversion hereabove referred to, presents a useful and effective means of combatting hypertension associated with that pressor agent.

It has been discovered that the compound of this invention is possessed of noteworthy activity in inhibiting angiotension I converting enzyme. Thus, in in vitro techniques designed to evince such activity this compound is highly effective. For example, it inhibits the pure converting enzyme isolated from rabbit lung tissue at a level of about 3.69 μm/l. It is, therefore, a notable angiotensin I converting enzyme inhibitor.

The compound of this invention is not limited to in vitro manifestations of its converting enzyme inhibiting propensity. Upon oral administration, a dose-dependent antihypertensive effect in acute aortic coarctation hypertensive rats is elicited. Oral dosage of about 17.5 mg/kg administered as a suspension in 0.5% Methocel solutions achieves a reduction of 30 mm Hg in mean arterial blood pressure in such rats.

The compound of this invention can be composed in a variety of dosage forms such as tablets, capsules, solutions and the like for convenient administration employing classical excipients and adjuvants with which there is no incompatibility. Such dosage forms contain from 10 to 500 mg of this compound in a unit dosage form in accordance with accepted pharmaceutical practice.

In order that this invention may be readily available to and understood by those skilled in the art, the following example describes the currently preferred method for the preparation thereof.

A. (±)-1,2,3,4-Tetrahydro-2-quinolinecarboxylic acid hydrochloride (26 g) was dissolved in a cold solution of sodium hydroxide (9.6 g) and water (125 ml). The solution was cooled with an ice bath and under vigorous stirring, a solution of sodium hydroxide (4.8 g) and water (60 ml), and chloroacetyl chloride (9.9 ml) were added dropwise. The mixture was stirred for 3 hours at room temperature and then potassium thiobenzoate (21 g) in water (120 ml) was added. This mixture was stirred at room temperature for 18 hours, cooled in an ice bath to 0°, and then acidified with concentrated hydrochloric acid. The product was extracted with chloroform and the extract dried over magnesium sulfate and concentrated to yield (±)-1-(2-benzoylthio-1-oxoethyl)-1,2,3,4-tetrahydro-2-quinolinecarboxylic acid; yield 20 g, m.p. 164°–168°.

(±)-1-(2-Benzoyl-1-oxoethyl)-1,2,3,4-tetrahydro-2-quinolinecarboxylic acid (29 g), concentrated ammonium hydroxide (53 ml) and water (106 ml) were combined and stirred at room temperature under nitrogen for 3 hours. After this time, the benzamine was filtered and water (150 ml) was added to the filtrate. This solution was extracted with ethyl acetate and then the aqueous phase was acidified with concentrated hydrochloric acid. The product was then extracted with chloroform and after drying over sodium sulfate and evaporation, (±)-1,2,3,4-tetrahydro-1-(2-mercapto-1-oxoethyl)-2-quinolinecarboxylic acid was obtained; yield 9.0 g, m.p. 85°–96°.

B. The compound of A. (7.0 g, 0.018 m), diisopropylethylamine (3.6 g, 0.028 m), dimethylformamide (150 ml), and diphenylphosphorylazide (7.7 g, 0.028 m) were combined and the solution was stirred for 5 hours at room temperature. The solution was then poured into ice water (2 l) and stirred for 1 hour. The resulting milky mixture was extracted with 4×300 ml of EtOAc. The EtOAc extracts were combined, washed 2×500 ml H$_2$O, dried (MgSO$_4$), filtered, and evaporated to a slurry. This slurry was washed with cold isopropanol (10 ml). The solid was collected by filtration, recrystallized twice with EtOAc (treated with charcoal) to give 1.7 g (26%); m.p. 185°–186° C.; R$_f$ 0.48 (10% HOAc/toluene); pmr was consistent with structure.

Anal. Calc'd. for C$_{12}$H$_{11}$NO$_2$S: C=61.78%; H=4.75%; N-6.00%; Found: C=61.97%; H=4.77%; N-5.94%

What is claimed is:

1. The compound 5,6-dihydro[1,4]thiazino[4,3-a]quinoline-1(2H),4(4aH)-dione.

* * * * *